(12) United States Patent
Wu et al.

(10) Patent No.: US 6,960,342 B2
(45) Date of Patent: Nov. 1, 2005

(54) **METHOD FOR INHIBITING PATHOGENIC FUNGI IN PLANTS USING *BACILLUS AMYLOLIQUEFACIENS***

(75) Inventors: Wen-Shi Wu, Taipei (TW); An-Long Chiou, Taipei (TW)

(73) Assignee: National Taiwan University, Taipei (TW)

( * ) Notice: Subject to any disclaimer, the term of this patent is extended or adjusted under 35 U.S.C. 154(b) by 77 days.

(21) Appl. No.: 10/241,591

(22) Filed: Sep. 12, 2002

(65) Prior Publication Data

US 2004/0052776 A1 Mar. 18, 2004

(51) Int. Cl.[7] .................. A01N 25/00; A01N 63/00; C12N 1/00; C12N 1/20
(52) U.S. Cl. ................. 424/93.46; 424/405; 435/252.5; 435/832
(58) Field of Search .............................. 435/252.5, 832; 424/93.46, 405, 93.1

(56) References Cited

U.S. PATENT DOCUMENTS 5,494,809 A * 2/1996 Tanaka et al. ............. 435/71.3

* cited by examiner

*Primary Examiner*—David M. Naff
*Assistant Examiner*—Deborah K. Ware
(74) *Attorney, Agent, or Firm*—Troxell Law Office, PLLC

(57) ABSTRACT

The present invention provides a novel *Bacillus amyloliquefaciens* strain that exhibits broad antifungal activity. The present invention also provides the use of the *Bacillus amyloliquefaciens* strain or an antifungal composition comprised of the novel strain for control of a broad range of fungal plant pathogens.

15 Claims, No Drawings

METHOD FOR INHIBITING PATHOGENIC FUNGI IN PLANTS USING *BACILLUS AMYLOLIQUEFACIENS*

TECHNICAL FIELD OF THE INVENTION

The present invention relates to fungicides and, more particularly, this invention relates to the finding that a novel strain of *Bacillus amyloliquefaciens*, B190, can inhibit a broad range of pathogenic fungi. The invention also relates to fungicidal compositions comprising the novel *Bacillus strain* and a mutant thereof having the same activity as the novel strain either alone, or in combination with other chemicals.

BACKGROUND OF THE INVENTION

In recent years, the acreage of lily has increased in Taiwan. For example, the acreages in 1995 and 1998 were 155 and 345 hectares, and the market value for these two years was NT$ 380. and 800 millions, respectively. Lily has become a potentially economic plant in Taiwan.

Lily gray mold caused by *Botrytis elliptica* (Berk) Cook was the most severe and destructive disease in the field and resulted in catastrophic economic losses. This phytopathogenic fungus leads to necrotic lesions and rots on leaves and flowers when there exist conducive environmental factors. Genus of *Botrytis* consists of 22 species. In Taiwan, *Botrytis* mainly comprises *B. cinerea* Pers, *B. elliptica* (Berk.) Cooke, *B. gladiolorum* Timmermans, *B. liliorum* Fujik and *B. allii-fistulosis* Sawada. Optimal temperatures and relative humidity for the growth of these species are 18 to 25° C. and 95 to 100%, respectively.

The gray mold disease of lily generally occurred from December to next March. For controlling this disease, fungicides were frequently used. However, several drawbacks were worthy of our attention. One of them is *Botrytis* spp. may develop resistance to specific fungicides like benzimidazoles, dicarboximides, diethofencarb or two sterol biosynthesis inhibitors within a relatively short period of time, thus increasing the difficulty of the gray mold control. Moreover, various kinds of pollution generated from the usage of the fungicides may become serious environmental problems. Therefore, an alternative solution such as biological control is a practical method because it is endurable, economical, stable and environmental compatible.

Based on the above descriptions, a competent antagonist isolated from lily is a good candidate for lily gray mold control. It is worthy to note that, however, the antagonist should have following abilities: allowing lily to adapt to the niche short of nutrients, tolerances to direct exposure of UV radiation and rush fluctuations of the temperature and relative humidity. In addition, the antagonist has to vie with other epiphytes successfully. A sound formulation that ensures the stability of the long-term storage of antagonists, enhances the ability of disease control and warrants the commercial value of biocontrol agents is also important.

Due to the gray mold disease not only attacking the lily but other valuable economic plants, it is important to inhibit the pathogenic fungus via biological control.

DISCLOSURE OF THE INVENTION

A novel strain of *Bacillus amyloliquefaciens* is provided that exhibits a broad range of antifungal activity. Also provided are methods of preventing or inhibiting plants from pathogenic fungi infections comprising the step of applying an effective amount of the novel strain of *Bacillus amyloliquefaciens*, B190, a mutant thereof having the same antifungal activity as the novel strain. In addition, one chemical at least should be combined with the novel bacterial strain and/or the mutant of the present invention. The novel *Bacillus amyloliquefaciens* strain, B190, can be provided as an emulsion or a wettable powder by mixing it with heavy mineral oil plus Tween 80 or kaolin, respectively.

MODES OF CARRYING OUT THE INVENTION

The present invention provides a novel strain of *Bacillus amyloliquefaciens* which exhibits broad antifungal activity. This novel strain is designated as B190 and was deposited at the Food Industry Research and Development Institute (FIRDI), Hsin-Chu, Taiwan, R.O.C., on Apr. 1, 2002 under accession number CCRC 910182. The invention also includes methods of preventing or inhibiting fungal diseases in plants using the novel strain or a mutant thereof having the same activity as the strain. In addition, at least one chemical can be combined with the strain and/or the mutant to prevent or inhibit infections caused by pathogenic fungi on plants.

Definitions

As used herein, "biological control" is defined as controlling of a pathogen by using its antagonist.

The term "fungus" or "fungi" includes a wide variety of nucleated, sporebearing organisms which are devoid of chlorophyll. Examples of fungi include yeasts, mildews, molds, rusts and mushrooms.

The term "bacteria" are prokaryotic organisms that does not have a distinct nucleus.

The term "fungicide" means a substance which has an ability to increase mortality or to inhibit growth rate of fungi.

The term "culture" refers to the propagation of organisms on or in various kinds of media.

The term "effective amount" means an amount sufficient to beneficial effects or desired results. In terms of prevention and inhibition, an "effective amount" is the amount sufficient to palliate, ameliorate, stabilize, slow or delay the progression of fungal disease states herein.

We describe a novel strain (B190) of *Bacillus amyloliquefaciens* or a mutant thereof that has broad antifungal activity. Further, we disclose a formulation, which is combined with the strain or a mutant thereof having the same antifungal activity, to help the strain or the mutant inhibit or kill fungi.

A sample of biological material has been deposited with the Food Industry Research and Development Institute, who address is 331 Shih-Pin Rd., Hsinchu, Taiwan, 300, R.O.C. The biological sample has identification number G120753983 and has patent deposit designation CCRC 910182 (CCRC: currently BCRC). The deposit was made on Apr. 1, 2002.

In another aspect, the present invention provides a method of preventing or inhibiting fungus infections on plants comprising applying an effective amount of the novel strain or the mutant.

The following examples are provided to illustrate the invention. These examples are not to be construed as limiting.

EXAMPLES

Example 1

Characterization of Strain B190
Identification of B190 as *Bacillus amyloliquefaciens*

BIOLOG system was used in the identification of the isolates of effective antagonists. "Gram's stain" was carried out before applying BIOLOG system with the software Microstation system release 3.50 (Biolog Inc., 3938 Trust Way, Hayward, Calif., U.S.A.). Basic triphenylmethane dyes (commonly crystal violet) and safranin O were used to stain the bacteria smear on slides to differentiate their stain reactions. Afterwards, all strains were subcultured onto nutrient agar (NA) and incubated for 16 h at 30° C. A single colony of each organism was taken from the nutrient agar and spread on Biolog universal growth medium (BUGM) supplemented with 1% glucose. Plates were incubated at 30° C. for 16 h. Single colony was removed and placed in a test tube containing 18 ml of 0.85% sterile NaCl for adjusting cell density to about $4.5 \times 10^8$ cells/ml. The suspension (150 µl) was dispensed to each well of the Biolog microplate. Plates were incubated at 30° C. and read by Biolog software (Release version 3.50).

Results showed that B190 was Gram's stain positive. In addition, BIOLOG results gave a similarity index of 0.781 positive identification as *Bacillus amyloliquefacies*.

Example 2
Antifungal Activity of *Bacillus amyloliquefaciens* B190
(A) Detached Leaves B190 was cultured on PDA plates at 25° C. with 12 h light for 5 days. A suspension of $1 \times 10^5$ cfu/ml was prepared therefrom and sprayed onto detached lily leaves. Detached leaves, approximately 9 cm long, were collected from 3-month-old plants (cultivars Acapulco, Casa Blanca and Marco Polo) and placed in petri dishes that lined with three pieces of moistened filter papers. Also, a spore suspension ($1 \times 10^3$ conidia/ml) of *Botrytis elliptica* was sprayed onto the detached lily leaves after spraying the antagonist. These inoculated leaves were incubated at 20° C. with 12 h light for 10 days. Thereafter, disease severity was assessed and based on a 0 to 4 scale (i.e. 0, no symptom; 1, 1–12%; 2, 13–25%; 3, 26–50%; 4, 51–100% leaf area covered with symptom). The disease severity was calculated by the sum of disease severity scale multiplying the number of diseased plants of the same category and divided by total number of tested plants×4. Each treatment consisted of 8 detached leaves in 4 replications. This test was repeated twice. All data were analyzed by Duncan's new multiple range test.

Please refer to Table 1. The antagonist B190 showed obvious inhibition to the infection caused by *Botrytis elliptica* on detached leaves of lily cultivars.

TABLE 1

| | Disease severity[a] Cultivars | | | | | |
|---|---|---|---|---|---|---|
| | Acapulco | | Casa Blanca | | Marco Polo | |
| Antagonist[b] | I[c] | II | I | II | I | II |
| C K | 4.00[d]a[e] | 4.00 a | 4.00 a | 4.00 a | 4.00 a | 4.00 a |
| B190 | 1.67 b | 0.83 b | 0.83 b | 0.83 b | 0.67 b | 0.68 b |

[a]Disease severity was assessed on a scale from 0 to 4, 0: no lesion was observed, 1: 1–12%, 2: 13–25%, 3: 26–50%, 4: more than 50% leaf areas were infected;
[b]The suspensions of antagonists (1 × 10$^5$ cfu/ml) were applied onto detached leaves of lily and incubated for 10 days before recording;
[c]I: the first trial, II: the second trial;
[d]The average of four replications, 2 leaves/replication;
[e]Data in the same column followed by different letters are significantly ( p = 0.05) different by Duncan's new multiple range test.

(B) In Greenhouse

Three cultivars of lily (Acapulco, Casa Blanca and Marco Polo) were planted in pots (18 cm in diameter) in November, 1998. Every pot had two plants of the same cultivar. When these plants grew to the flowering stage in the greenhouse, they were used for bioassay. The preparation and inoculation of antagonist and pathogen were the same as aforementioned with one modification: 5 ml of inoculum was sprayed onto each entire plant instead of applying 1 ml of inoculum onto detached leaves. The inoculated plants were kept in the greenhouse at 18–25° C. for 10 days before recording. Each treatment consisted of 8 plants in 4 replications. This experiment was based upon randomized complete block design. This test was repeated twice and analyzed by Duncan's new multiple range test.

As shown in Table 2, *Bacillus amyloliquefaciens* B190 significantly inhibited the infections caused by *Botrytis elliptica*.

TABLE 2

| | Disease severity[a] Cultivars | | | | | |
|---|---|---|---|---|---|---|
| | Acapulco | | Casa Blanca | | Marco Polo | |
| Antagonist[b] | I[c] | II | I | II | I | II |
| C K | 2.19[b]a[e] | 2.75 a | 3.75 a | 3.75 a | 2.58 a | 3.50 a |
| B190 | 0 b | 0.25 b | 0.50 b | 0.25 b | 0 b | 0.25 b |

[a]Disease severity was assessed on a scale from 0 to 4, 0: no lesion was observed, 1: 1–12%, 2: 13–25%, 3: 26–50%, 4: more than 50% leaf areas were infected;
[b]The suspensions of antagonists (1 × 10$^5$ cfu/ml) were applied onto lily plants and incubated for 10 days before recording;
[c]I: the first trial, II: the second trial;
[d]The average of four replications, 2 plants/replication;
[e]Data in the same column followed by different letters are significantly ( p = 0.05 ) different by Duncan's new multiple range test.

(C) Field Trials

Lily fields in Taipei and I-Lan counties were selected for this experiment. Suspensions of the B190 and *Botrytis elliptica* were adjusted to about $1 \times 10_5$ cfu/ml and $1 \times 10^3$ conidia/ml, respectively, before application. 100 ppm of flusilazole (37% Emulsion, Du Pont, USA) was used for comparison. After spraying B190 or flusilazole by sprayer (MS sprayer, Taiwan), 5 ml of the spore suspension of *Botrytis elliptica* was sprayed onto each 100-day-old lily plant. A total of three sprays at 10-day intervals were applied. Each treatment consisted of 100 plants with 4 replicates. Every replicate was planted on a plot, which was 30 m long and 2 m wide. All the treatments were arranged based on randomized complete block design. Two weeks after the last spray, disease severity was assessed and analyzed as above-mentioned.

As shown in Table 3, the *Bacillus amyloliquefacies* B190 was as effective as flusilazole in controlling lily gray mold in two different field locations.

TABLE 3

| | Disease severity[a] | |
|---|---|---|
| Treatment[b] | I-Lan | Taipei |
| Health-CK | 0.83[c]b[d] | 0.22 c |
| Disease-CK | 2.20 a | 1.47 a |
| B. amyloliquefaciens B190 | 1.10 b | 0.36 bc |
| Flusilazole | 0.80 b | 0.31 bc |

[a]Disease severity was assessed on a scale from 0 to 4, 0: no lesion was observed, 1: 1–12%, 2: 13–25%, 3: 26–50%, 4: more than 50% leaf areas were infected;

TABLE 3-continued

|  | Disease severity[a] | |
|---|---|---|
| Treatment[b] | I-Lan | Taipei |

[b]The suspensions of antagonists (1 × 10$^5$ cfu/ml) or 100 ppm flusilazole were applied onto lily plants at two different places for three times, and disease severity was recorded 14 days after the last application;
[c]The average of four replications, 25 plants/replication;
[d]Data in the same column followed by different letters were significantly (p = 0.05) different by Duncan's new multiple range test.

Example 3
Antifungal Activity of Various *Bacillus amyloliquefaciens* B190 Formulations on *Botrytis elliptica* Infected Lilies (A) In Greenhouse

*Bacillus amyloliquefaciens* B190 was cultured in a flask containing 1% rice chaff and 99% de-ion water. The flask was then positioned on a rotary shaker located in an incubator. B190 was incubated at 25±5° C. for 3 days. Thereafter, the B190-containing solution was filtered for application in the following experiments.

Different chemicals or adjuvants were added to the B190-containing filtrate for investigating their inhibitive capability on *Botrytis elliptica* infected lilies in greenhouse. The chemicals include 0.025% Ca(OH)$_2$, 0.05% Na$_2$CO$_3$, 0.025% NH$_4$NO$_3$ and 0.025% K$_2$HPO$_4$. The adjuvants comprise 0.1% Tween 80 and 0.05% mineral oil.

Unformulated *B. amyloliquefaciens* B190 and 100 p.p.m. flusilazole were used as controls. In addition, uninoculated and inoculated lily plants with *B. elliptica* were also included as controls. Applications of these treatments were carried out when flowering tissues reached 30 to 50 mm in diameter. Treatments were applied three times with intervals of 10 days. Thereafter, 5 ml of *B. elliptica* spore suspension (1×10$^3$ conidia/ml) was inoculated on lily plants except the uninoculated control. Each different treatment had four replicates, and 5 lily plants were applied in every replicate. All treatments were arranged in a randomized complete block design. After inoculating *B. elliptica* for ten days, disease severity was scored as described above.

Please refer to Table 4. All of the different treatments inhibited lily gray mold significantly (p=0.05) while comparing with the inoculated control (known as Disease-CK). In addition, there were better effects of mixing *B. amyloliquefaciens* B190 with 0.025% calcium hydroxide plus 0.05% sodium carbonate, 0.025% calcium hydroxide plus 0.025% ammonium nitrate, or 0.1% Tween 80 plus 0.05% mineral oil than that of mixing B190 without these chemicals.

TABLE 4

| Treatment[a] | Disease severity[b] |
|---|---|
| Health-CK | 0[c] g[d] |
| Disease-CK | 2.69 a |
| *B. amyloliquefaciens* B190 | 0.63 cd |
| A + B | 0.63 cd |
| A + C | 1.25 b |
| A + B + C + D | 0.57 cde |
| Adjuvants | 0.75 c |
| (A + B) + B190 | 0.25 f |
| (A + C) + B190 | 0.75 c |
| (A + B + C + D) + B190 | 0.50 cdef |
| Adjuvants + B190 | 0.40 def |
| Flusilazole | 0.32 ef |

TABLE 4-continued

| Treatment[a] | Disease severity[b] |
|---|---|

[a]The suspensions of *B. amyloliquefaciens* B190 (1 × 10 cfu/ml) were applied onto lilies for 3 times (10 days/interval); (A) 0.025% Ca(OH)$_2$, (B) 0.05% Na$_2$CO$_3$, (C) 0.025% NH$_4$NO$_3$, (D) 0.025% K$_2$HPO$_4$; Adjuvants were 0.1% Tween 80 and 0.05% mineral oil. Ten days after the last application, the disease severity of each treatment was recorded;
[b]Disease severity was assessed on a scale from 0 to 4, 0: no lesion was observed, 1: 1–12%, 2: 13–25%, 3: 26–50%, 4: more than 50% leaf areas were infected;
[c]Mean, the average of eight replications, 80 plants/treatment;
[d]Data in the same column followed by different letters were significantly (p = 0.05) different by Duncan's new multiple range test.

(B) In Field

*Bacillus amyloliquefaciens* B190 was cultured in a flask containing 1% rice chaff and 99% de-ion water. Then the flask was positioned on a rotary shaker located in an incubator. B190 was incubated at an ambient temperature of 25±5° C. for 3 days. Thereafter, the cultured B190 was collected by means of centrifugation (3000 rpm/10 minutes; Tomy CM-60 RN, Seiko, Japan). The pellet mixed with 1% (w/v) kaolin was used as a wettable powder (WP). The pellet mixed with 0.025% (v/v) heavy mineral oil and 0.1% Tween 80 was served as an emulsion (E).

Different chemicals or adjuvants were added to the wettable powder, emulsion or B190-containing filtrate as described above for investigating their inhibitory ability on lilies in the field. These chemicals include 0.025% Ca(OH)$_2$, 0.05% Na$_2$CO$_3$, 0.025% NH$_4$NO$_3$ and 0.025% K$_2$HPO$_4$. The adjuvants comprise 0.1% Tween 80 and 0.05% mineral oil.

Unformulated *B. amyloliquefaciens* B190 and 100 p.p.m. flusilazole were used as controls. In addition, uninoculated and inoculated lily plants with *B. elliptica* were also included as controls. Applications of these treatments were carried out when flowering tissues reached 100 to 120 mm in diameter. Treatments were applied three times with intervals of 10 days. Thereafter, 5 ml of *B. elliptica* spore suspension (1×10$^3$ conidia/ml) was inoculated in lily plants except the uninoculated control. Each different treatment had eight replicates, and 80 lily plants were applied in every replicate. All treatments were arranged in a randomized complete block design. After inoculating *B. elliptica* for ten days, disease severity was scored as described above.

As shown in Table 5, in which all the treatments significantly (p=0.05) controlled the lily gray mold in the fields. The effect of treating lilies with *B. amyloliquefaciens* B190, 0.025% calcium hydroxide plus 0.05% sodium carbonate or mixture of *B. amyloliquefaciens* B190, 0.025% calcium hydroxide and 0.05% sodium carbonate (in the state of emulsion) was significantly (p=0.05) different from those of inoculating lilies with *Botrytis elliptica* alone (known as Diseased-CK) in two different field trials. A similar result occurred when treating lily plants with mixtures of *B. amyloliquefaciens* B190, 0.025% calcium hydroxide and 0.05% sodium carbonate (in the state of wettable powder) in one field trial. In addition, as shown in Table 5, applying adjuvants alone or the combination of *B. amyloliquefaciens* B190 with adjuvants on lily plants were significantly effective when comparing with Diseased-CK.

TABLE 5

| Treatment[b] | Disease severity[a] | |
|---|---|---|
| | I[c] | II |
| Health-CK | 0.18[d][e] | 0.11 c |
| Diseased-CK | 1.01 a | 1.82 a |
| B. amyloliquefaciens B190 | 0.32 cd | 0.39 bc |
| AB | 0.32 cd | 0.57 b |
| B190 + AB (E) | 0.23 cd | 0.36 bc |
| B190 + AB (WP) | —[f] | 0.44 bc |
| ABCD | 0.53 b | — |
| B190 + ABCD | 0.55 b | — |
| Adjuvants | 0.39 bc | — |
| B190 + Adjuvants | 0.37 bc | — |
| Flusilazole | 0.23 cd | 0.39 bc |

[a]Disease severity was assessed on a scale from 0 to 4, 0: no lesion was observed, 1: 1–12%, 2: 13–25%, 3: 26–50%, 4: more than 50% leaf areas were infected;
[b](A), 0.025% $Ca(OH)_2$; (B), 0.05% $Na_2CO_3$; (C), 0.025% $NH_4NO_3$; (D), 0.025% $K_2HPO_4$; and (E), 0.1% Tween 80; B. amyloliquefaciens B190 + AB (E): B. amyloliquefaciens B190 mixed with A, B and 0.05% mineral oil (heavy) ; B. amyloliquefaciens B190 + AB (WP): B. amyloliquefaciens B190 mixed with A, B and 1% kaolin; Adjuvants was 0.1% Tween 80 and 0.05% mineral oil;
[c]The suspensions of B. amyloliquefaciens B190 (1 × 10[5] cfu/ml) were applied onto lilies for 3 times (10 days/interval). Fourteen days after the last application, the disease severity of each treatment was recorded. I: two trials in I-Lan county; II: two trials in NTU experimental farm;
[d]Mean, the average of four replications, 320 plants/treatment;
[e]Data in the same column followed by different letters were significantly (p = 0.05) different by Duncan's new multiple range test;
[f]No test.

Example 4

Survival of *Bacillus amyloliquefaciens* B190

It is reported that a microorganism in a biocontrol agent used for plant disease control should survive at least 6 months. Please refer to Table 6, in which effects of different constituents on survival of *Bacillus amyloliquefaciens* B190 were investigated. Results showed that B190 in the emulsified state mixing with 0.025% $Ca(OH)_2$ and 0.05% $Na_2CO_3$ survived for 9 months at least without decline. Further, B190 incubated in de-ion water containing 1% rice chaff had an ability to survive over 16 months.

TABLE 6

| Treatment | Concentration | Colony forming unit (1 × 10[6])/ml Months of storage | | | | |
|---|---|---|---|---|---|---|
| | | 0[1] | 1 | 2 | 3 | 4 |
| B190 : $H_2O$ | 3:7, v/v | 68 b[2]M[3] | 380 bcC | 390 bB | 638 aA | 133 dK |
| B190 : $H_2O$ | 7:3, v/v | 175 aL | 494 bC | 524 aB | 631 aA | 150 cO |
| B190 + 0.025% $Ca(OH)_2$ | | 35 cC | 21 bcO | 101 cdM | 250 cB | 461 aA |
| B190 + 0.05% $Na_2CO_3$ | | 175 aD | 478 bcA | 47 dO | 83 eJ | 234 bB |
| B190 + 0.025% Mineral oil | | 171 aE | 589 aA | 590 aA | 257 cB | 236 bC |
| B190 + 0.1% Tween 80 | | 182 aB | 497 bA | 147 cC | 108 dF | 84 eI |
| B190 : Const.[4] | 3:7, v/v | 6 dB | 48 dA | 2 hD | 5 eBC | 1 fD |
| B190 : Const.[4] | 7:3, v/v | 83 bJ | 410 bcF | 545 aA | 432 bD | 452 aB |
| B190 : Const.[5] | 3:7, v/v | 6 dB | 100 cdA | 1 hD | 1 eD | 2 fCD |
| B190 : Const.[5] | 7:3, v/v | 10 dC | 372 bcA | 13 hB | 13 eB | 5 fE |

| Treatment | Colony forming unit (1 × 10[6])/ml Months of storage | | | | | |
|---|---|---|---|---|---|---|
| | 5 | 6 | 7 | 8 | 9 | 10 |
| B190 : $H_2O$ | 138 fJ | 139 dJ | 130 bL | 138 bJ | 148 cI | 179 cD |
| B190 : $H_2O$ | 189 cH | 220 bD | 180 aJ | 192 aG | 219 aD | 208 aE |
| B190 : $Ca(OH)_2$ | 210 bC | 206 bD | 100 cM | 124 bcL | 157 bH | 191 bE |
| B190 + $Na_2CO_3$ | 184 dC | 121 eE | 82 dJ | 76 dL | 66 eH | 79 dK |
| B190 + Mineral oil | 164 eE | 182 cD | 103 cF | 78 cdHI | 79 deH | 74 deIJ |
| B190 + Tween 80 | 120 gE | 128 deD | 43 eM | 89 cG | 85 dHI | 78 dK |
| B190 : Const. | 2 hD | 4 fC | 1 fD | 4 eC | 5 fBC | 4 fC |
| B190 : Const. | 420 aE | 446 aC | 118 bcG | 108 bcH | 87 dI | 66 eK |
| B190 : Const. | 3 hC | 3 fCD | 2 fCD | 1 eD | 2 fCD | 1 fD |
| B190 : Const. | 7 hD | 1 fG | 2 fFG | 3 eF | 2 fFG | 2 fFG |

| Treatment | Colony forming unit (1 × 10[6])/ml Months of storage | | | | | |
|---|---|---|---|---|---|---|
| | 11 | 12 | 13 | 14 | 15 | 16 |
| B190 : $H_2O$ | 132 cK | 175 bE | 168 abG | 170 bF | 159 aH | 148 bI |
| B190 : $H_2O$ | 178 aK | 194 aF | 182 aI | 180 aJ | 162 aM | 157 aN |
| B190 : $Ca(OH)_2$ | 160 bG | 163 cF | 160 bG | 155 cI | 152 bJ | 145 cK |
| B190 : $Na_2CO_3$ | 70 deM | 85 fI | 91 cH | 96 dF | 95 cFG | 94 dG |
| B190 + Mineral oil | 73 dJ | 94 dG | 91 cG | 92 deG | 91 cdG | 93 dG |
| B190 + Tween 80 | 76 dL | 89 eG | 86 cH | 89 eG | 82 dJ | 76 eE |

TABLE 6-continued

| B190 : Const. | 5 fBC | 4 gC | 4 eC | 5 gBC | 2 fD | 2 gD |
| --- | --- | --- | --- | --- | --- | --- |
| B190 : Const. | 65 eK | 12 hN | 13 dMN | 16 fL | 14 eM | 17 fL |
| B190 : Const. | 2 fCD | 1 hD | 1 fD | 1 hD | 2 fCD | 1 gD |
| B190 : Const. | 1 fG | 1 hG | 2 fFG | 2 hFG | 2 fFG | 2 gFG |

[1]*Bacillus amyloliquefaciens* B190 cultured in a liquid synthetic medium was counted by means of colony forming unit after storage for different months. This experiment was repeated twice;
[2]Data in the same small letter in each column followed by different letters were significantly ($p = 0.05$) different by Duncan's new multiple range test;
[3]Data in the same capital letter in each row followed by different letters were significantly ($p = 0.05$) different by Duncan's new multiple range test;
[4]Constituents were $Ca(OH)_2$, $Na_2CO_3$, mineral oil and Tween 80 (1:1:1:1, w/v or v/v);
[5]Constituents were $Ca(OH)_2$, $Na_2CO_3$, kaolin and Tween 80 (1:1:1:1, w/v or v/v).

Example 5
Inhibitory Activity of *Bacillus amyloliquefaciens* B190 on Other Pathogenic Fungi To determine inhibitory effects of *Bacillus amyloliquefaciens* B190 on other pathogenic fungi, experiments were carried out by dual and concomitant cultures. Results showed that the novel strain, B190, revealed its antifungal activity on a broad range of plant species. Except *Botrytis elliptica,* pathogenic fungi inhibited by B190 included *Alternaria brassicicola, Alternaria protenta, Alternaria solani, Alternaria tagetica, Alternaria zinniae, Bipolaris austrialiensis, Curvularia lunata, Curvularia senegalensis, Fusarium lateritium, Phytophthora parasitica, Pythium sylvaticum, Rhizoctonia solani* AG-4, *Sclerotium rolfsii, Sclerotinia sclerotiorum,* and *Stemphylium vesicarium* (data not shown).

Although the preferred embodiment of this invention has been disclosed for illustrative purpose, those skilled in the art will appreciate that various modifications, additions and substitutions are possible, without departing from the scope and spirit of the invention as described in the accompanying claims.

What is claimed is:

1. A formulation with an antifungal ability comprising a biologically pure culture of *Bacillus amyloliquefaciens* strain B190 or a mutant thereof having a same antifungal ability as said strain on plants.

2. The formulation of claim 1, wherein the formulation is an aqueous solution.

3. The formulation of claim 1, wherein the formulation is an emulsion.

4. The formulation of claim 1, wherein the formulation is a wettable powder.

5. The formulation of claim 1, further comprising $Ca(OH)_2$, $Na_2CO_3$, $NH_4NO_3$, $K_2HPO_4$, mineral oil, Tween 80 or a combination thereof.

6. A formulation with an antifungal ability comprising a biologically pure culture of *Bacillus amyloliquefaciens* strain B190 or a mutant thereof having a same antifungal ability as said strain, wherein the formulation inhibits at least one of fungi of the group consisting of *Botrytis elliptica, Alternaria brassicicola, Alternaria protenta, Alternaria solani, Alternaria tagetica, Alternaria zinniae, Bipolaris austrialiensis, Curvularia lunata, Curvularia senegalensis, Fusarium lateritium, Phytophthora parasitica, Pythium sylvaticum, Rhizoctonia solani* AG-4, *Sclerotium rolfsii, Sclerotinia sclerotiorum* and *Stemphylium vesicarium.*

7. The formulation of claim 6, wherein the formulation is an aqueous solution.

8. The formulation of claim 6, wherein the formulation is an emulsion.

9. The formulation of claim 6, wherein the formulation is a wettable powder.

10. The formulation of claim 6, further comprising $Ca(OH)_2$, $Na_2CO_3$, $K_2HPO_4$, mineral oil, Tween 80 or a combination thereof.

11. A formulation with an antifungal ability comprising a biologically pure culture of *Bacillus amyloliquefaciens* strain B190 or a mutant thereof having a same antifungal ability as said strain, wherein the formulation inhibits at least one of fungi of the group consisting of *Botrytis elliptica, Alternaria brassicicola, Alternaria protenta, Alternaria solani, Alternaria tagetica, Alternaria zinniae, Bipolaris austrialiensis, Curvularia lunata, Curvularia senegalensis, Fusarium lateritium, Phytophthora parasitica, Pythium sylvaticum, Rhizoctonia solani* AG-4, *Sclerotium rolfsii, Sclerotinia sclerotiorum* and *Stemphylium vesicarium* on plants.

12. The formulation of claim 11, wherein the formulation is an aqueous solution.

13. The formulation of claim 11, wherein the formulation is an emulsion.

14. The formulation of claim 11, wherein the formulation is a wettable powder.

15. The formulation of claim 11, further comprising $Ca(OH)_2$, $Na_2CO_3$, $NH_4NO_3$, $K_2HPO_4$, mineral oil, Tween 80 or a combination thereof.

* * * * *